US00PP08219P

United States Patent [19]

Vardi et al.

[11] Patent Number: Plant 8,219

[45] Date of Patent: May 4, 1993

[54] MANDARIN TREE NAMED 'WINOLA'

[75] Inventors: Aliza Vardi; Pinchas Spiegel-Roy, both of Ramat Gan; Avraham Elchanati, Holon, all of Israel

[73] Assignee: State of Israel, Agricultural Research Organization, Bet Dagan, Israel

[21] Appl. No.: 666,283

[22] Filed: Mar. 8, 1991

[30] Foreign Application Priority Data

Mar. 8, 1990 [IL] Israel ..... 1557/90

[51] Int. Cl.[5] ..... A01H 5/00

[52] U.S. Cl. ..... Plt./45

[58] Field of Search ..... Plt./45

*Primary Examiner*—James R. Feyrer

*Attorney, Agent, or Firm*—Browdy and Neimark

[57] ABSTRACT

A new variety of mandarin citrus, named "Winola", is distinguished by a triploid chromosome number (3n=27), anthers bearing pollen with low viability, fruit which is seedless, leaves which are thicker and stiffer than Temple, thorns borne mainly in the lower part of the tree and fruit which is predominantly inside the canopy. Winola resulted from a controlled pollination cross-breeding between Wilking as a seed bearing parent and Minneola as a pollen parent. The fruit surface is wrinkled with an orange-red color and bears conspicuous, but sparsely distributed rind oil glands. The thickness of the rind is medium to thick, and adherence of the flesh to the rind varies from strong to semiadherent to easy peeling depending on the root stock and fruit maturity. Neither areola nor navel are present, and the fruit flesh is juicy, aromatic and of excellent taste, with segments of the fruit being easily separated.

1 Drawing Sheet

FIELD OF THE INVENTION

This invention is directed to a novel variety of mandarin tree of the genus Citrus L. which resulted from a controlled pollination between a seed bearing parent Wilking mandarin and a pollen parent Minneola tangelo, made at the Agricultural Research Organization, the Volcani Center, Bet Dagan, Israel.

BACKGROUND OF THE INVENTION

The objective in breeding the present novel variety, assigned the denomination WINOLA, was to obtain a late ripening seedless mandarin citrus. In the spring of 1979 a controlled pollination cross between Wilking mandarin (resulting from a cross of King×Willowleaf (Mediterranean) made in 1915 and reported by H. B. frost in *Calif. Agr. Exp. Sta. Bull,* 1935, 597–601.) as a seed bearing parent and Minneola tangelo (resulting from a cross between Duncan grapefruit and Dancy mandarin produced in Florida by the USDA and named and released in 1931) as a pollen parent was made at the Agricultural Research Organization, the Volcani Center, Bet Dagan, Israel. The fruits were collected in November 1979. Seeds of these fruits were extracted and subsequently germinated during January 1980. About 16 seedlings were top grafted on a mature Valencia orange scion grafted on a Troyer rootstock growing in an experimental grove in the Acre Experimental Station, Acre, Israel.

The first fruits were observed in March 1984 and a second observation was made in February–March 1985. One of the 16 scions was selected and numbered 1-5-1. The fruits of this selection were orange red colored, seedless and they were fully ripe in March.

Budwood was taken from the above mentioned selection and top-grafted in the spring of 1985 on two Valencia orange scions grafted on Sour Orange rootstocks growing in an experimental grove of the Agricultural Research Organization, The Volcani Center, Bet Dagan, Israel. The first crop of these trees was obtained in 1988. The yield was good and the fruit had an excellent flavor.

In the spring of 1988, five additional Winola trees grafted on Troyer rootstocks in the experimental grove of the Agricultural Research Organization, The Volcani Center, were also grafted with budwood from the above mentioned tree.

SUMMARY OF THE INVENTION

The present invention provides a novel variety of mandarin citrus characterized by a triploid chromosome number (3n=27), anthers bearing pollen with low viability and fruit which is seedless.

BRIEF DESCRIPTION OF THE DRAWINGS

Distinctive characteristics of the new variety are exemplified in the accompanying illustrations in which:

FIG. 1 shows whole fruit of the new variety illustrating the exterior of the fruit, as well as traverse mid-sections of the fruit in a plane substantially perpendicular to the axis of the fruit, illustrating the seedless interior of the fruit; and FIG. 2 shows the tree and the leaf canopy of the new variety.

PLANT CHARACTERISTICS

The following is a detailed description of the new mandarin citrus variety based on observations made under conventional grove conditions.

Tree: The tree is small to medium sized, up to 4 meters in height and moderately vigorous. The lower inner parts of the tree and juvenile parts of water shoots are thorny (large thorns), while flowering branches have small thorns. Spines are located near the leaf base. The larger spines, especially on the main juvenile part of the tree, can be up to 6 cm long and 4 mm in diameter at the basal end. Thorns on flowering and fruit bearing branches are 2–4 cm long with a tendency to nearly thornlessness. Main branches and juvenile branches when young have a drooping attitude and fruit is found predominantly inside the leaf canopy. Young shoots have no anthrocyanin coloration even at the tip. Bark of new wood is green, while bark of old wood takes on a brown-gray color. Pruning is required, especially at the non-fruiting stage, due to the drooping growth attitude of the tree.

Leaf: Leaves are small to medium size, very firm, without undulation, have a concave cross section, and are pointed at the base and at the apex. Petioles are without wings or have rudimentary wings.

Flower: Flowers have normal citrus characteristics, are small to medium size without any trace of anthocyanin coloration and the flowers are borne singly. The date of flowering is about the same as most Citrus cultivars grown in Israel approximately early April. Anthers have a normal shape, however pollen viability is low and anthers typically do not dehisce. Pollen viability was tested at The Agricultural Research Organization, The Volcani Center and found to be low.

Ploidy: Triploid (3n=27) as determined by microscopic examination performed at The Agricultural Research Organization, The Volcani Center.

Fruit: Fruit is seedless, globose, and medium sized with a moderately depressed stalk end and a depressed distal end. The fruit is typically between 6.0 and 7.0 cm in diameter, and individual fruit weigh between 115 and 162 grams. The fruit surface is wrinkled with an orange-red color between 32A and 33A on The Royal Horticultural Society of London Colour Chart, and bears conspicuous, but sparsely distributed rind oil glands. The thickness of the rind is medium to thick (3–4 mm) and the adherence of the flesh to the rind varies from strong to semi-adherent to easy peeling depending on rootstock and fruit maturity. A style does not persist and neither an areola or navel are present. The fruit flesh is juicy (juice quantity is approximately 60%). aromatic and of excellent taste. The segments of the fruit are easily separated and the fruits are typically seedless with occasionally one seed, usually aborted, in trees adjacent to other cultivars.

On the basis of the above fruit characteristics the tree was classified as a mandarin.

The fruit typically ripens and reaches maximum fruit quality between the end of February and the middle of March. At this time the fruit has a distinct orange aroma. Ripening of tissues within the fruit is uniform and substantially all of the fruit ripens between the end of February and mid-March. Fruit held on the tree after March does not regreen, but looses quality until it falls at the beginning of May.

Fruit-set in block is normal and it is therefore assumed that no pollinator is required for commercial fruit-set. The yield per tree is approximately 80–100 Kg.

Winola has a tendency to biennial bearing after heavy cropping and late in season picking.

The results of a quality test conducted on representative ripe fruit of the novel variety are as follows:

Total soluble solids (TSS)—15.0%.
Acid content—1.5%.
TSS/acid ratio—10.0.

I claim:

1. A novel variety of mandarin citrus substantially as herein shown and described, characterized by a triploid chromosome number (3n=27), anthers bearing pollen with low viability and fruit which is seedless.

* * * * *

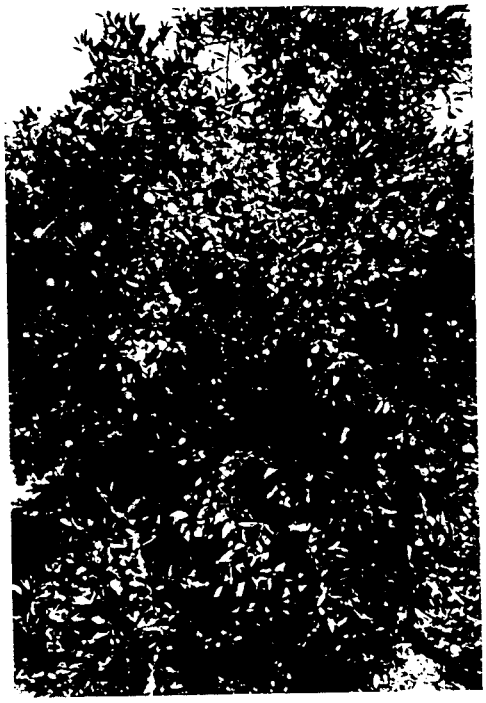

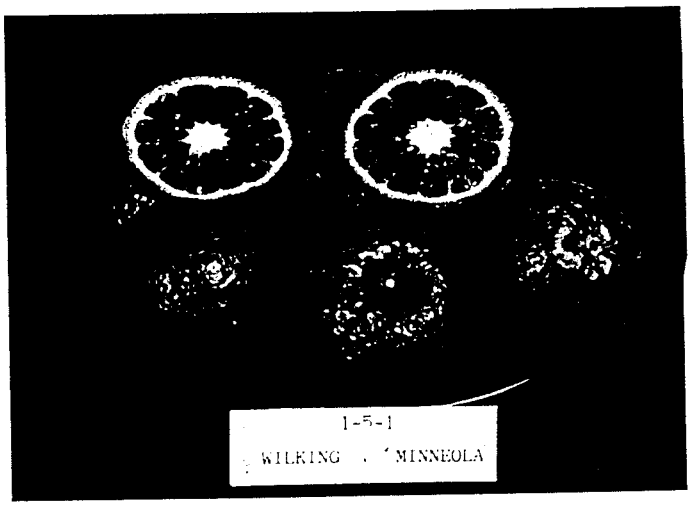
1-5-1
WILKING
MINNEOLA